(12) United States Patent
Sugie et al.

(10) Patent No.: US 11,804,134 B2
(45) Date of Patent: Oct. 31, 2023

(54) CONTROL DEVICE, SYSTEM, COMPUTER-READABLE MEDIUM, AND MATCHING METHOD

(71) Applicant: TOYOTA JIDOSHA KABUSHIKI KAISHA, Toyota (JP)

(72) Inventors: Yui Sugie, Nagoya (JP); Hikaru Gotoh, Nagoya (JP); Hiroki Kido, Miyoshi (JP); Shuichi Sawada, Nagoya (JP); Genshi Kuno, Kasugai (JP); Katsuhiro Ohara, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 157 days.

(21) Appl. No.: 17/532,596

(22) Filed: Nov. 22, 2021

(65) Prior Publication Data

US 2022/0254255 A1  Aug. 11, 2022

(30) Foreign Application Priority Data

Feb. 5, 2021  (JP) ................. 2021-017772

(51) Int. Cl.
*G08G 1/14* (2006.01)
*G16H 50/70* (2018.01)

(52) U.S. Cl.
CPC ............. *G08G 1/143* (2013.01); *G16H 50/70* (2018.01)

(58) Field of Classification Search
CPC ........ G08G 1/143; G16H 50/70; G16H 20/70; G06Q 50/265; G06Q 50/22; G06Q 50/01; G06F 16/2458; H04W 4/21; H04W 4/90; H04W 76/50
See application file for complete search history.

(56) References Cited

U.S. PATENT DOCUMENTS

| | | | |
|---|---|---|---|
| 6,735,568 B1 * | 5/2004 | Buckwaiter ............ | G06Q 50/01 705/319 |
| 7,085,806 B1 * | 8/2006 | Shapira ................... | G06Q 30/08 709/202 |
| 8,606,787 B1 * | 12/2013 | Asgekar ................ | G06F 16/285 707/737 |
| 11,651,405 B1 * | 5/2023 | Gray ...................... | A45C 11/24 705/26.5 |

(Continued)

FOREIGN PATENT DOCUMENTS

JP  2013-113070 A  6/2013

*Primary Examiner* — Ryan W Sherwin
(74) *Attorney, Agent, or Firm* — Oliff PLC

(57) ABSTRACT

A control device includes: a communication unit that receives input data from a terminal device of a first member who is a member of a first family staying in a vehicle, the input data indicating a family composition and a family stress for the first family; and a control unit that searches a database in which data indicating the family composition and the family stress for each of a plurality of families staying in individual vehicles is registered, using the input data received by the communication unit as a search key, selects a second family from the families based on a search result obtained, and causes the communication unit to transmit notification data that notifies the first member of information for establishing a relationship with a second member who is a member of the second family selected.

20 Claims, 9 Drawing Sheets

(56) References Cited

U.S. PATENT DOCUMENTS

| | | | |
|---|---|---|---|
| 2009/0030985 A1* | 1/2009 | Yuan | H04L 67/306 |
| | | | 709/204 |
| 2011/0099196 A1* | 4/2011 | Farsedakis | G06F 16/24573 |
| | | | 707/769 |
| 2013/0159333 A1* | 6/2013 | Assam | G06Q 50/01 |
| | | | 707/758 |
| 2013/0297692 A1* | 11/2013 | Raji | H04L 65/403 |
| | | | 709/204 |
| 2014/0025760 A1* | 1/2014 | Shore | H04L 51/212 |
| | | | 709/206 |
| 2017/0287094 A1* | 10/2017 | Nidiffer | G06Q 50/26 |

* cited by examiner

FIG. 2

| FAMILY ID | FAMILY COMPOSITION | FAMILY STRESS | ... |
|---|---|---|---|
| 1 | ONE CHILD<br>TWO ELDERLY PERSONS<br>ONE PET | CHILDCARE<br>ELDERLY CARE AND ILLNESS OF ELDERLY PERSONS<br>PET CARE | ... |
| 2 | ONE CHILD<br>ONE ELDERLY PERSON<br>TWO PETS | CHILDCARE<br>ELDERLY CARE<br>PET CARE AND ILLNESS OF PET | ... |
| 3 | NO CHILD<br>NO ELDERLY PERSON<br>NO PET | NO FAMILY STRESS | ... |
| ... | ... | ... | ... |

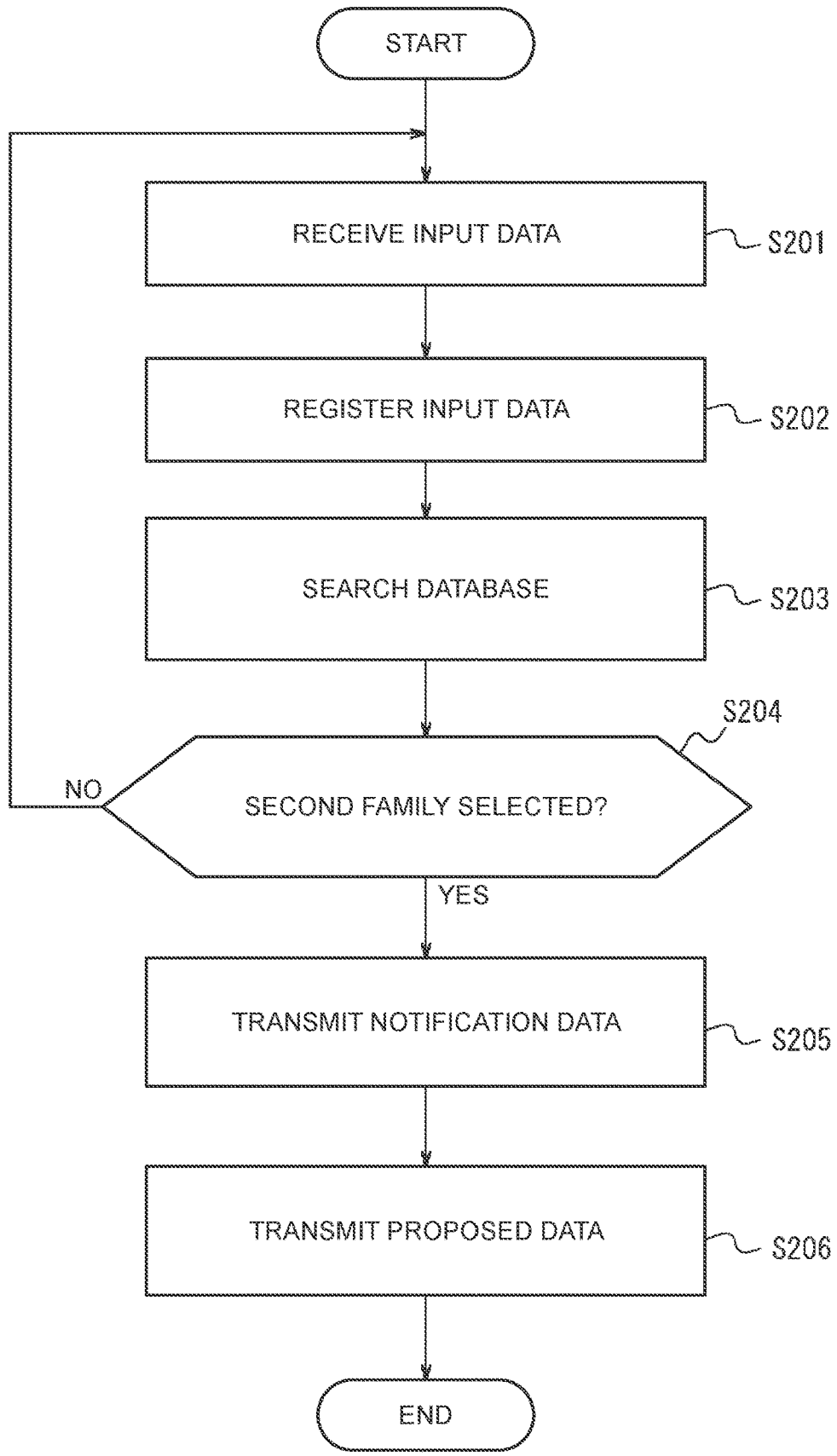

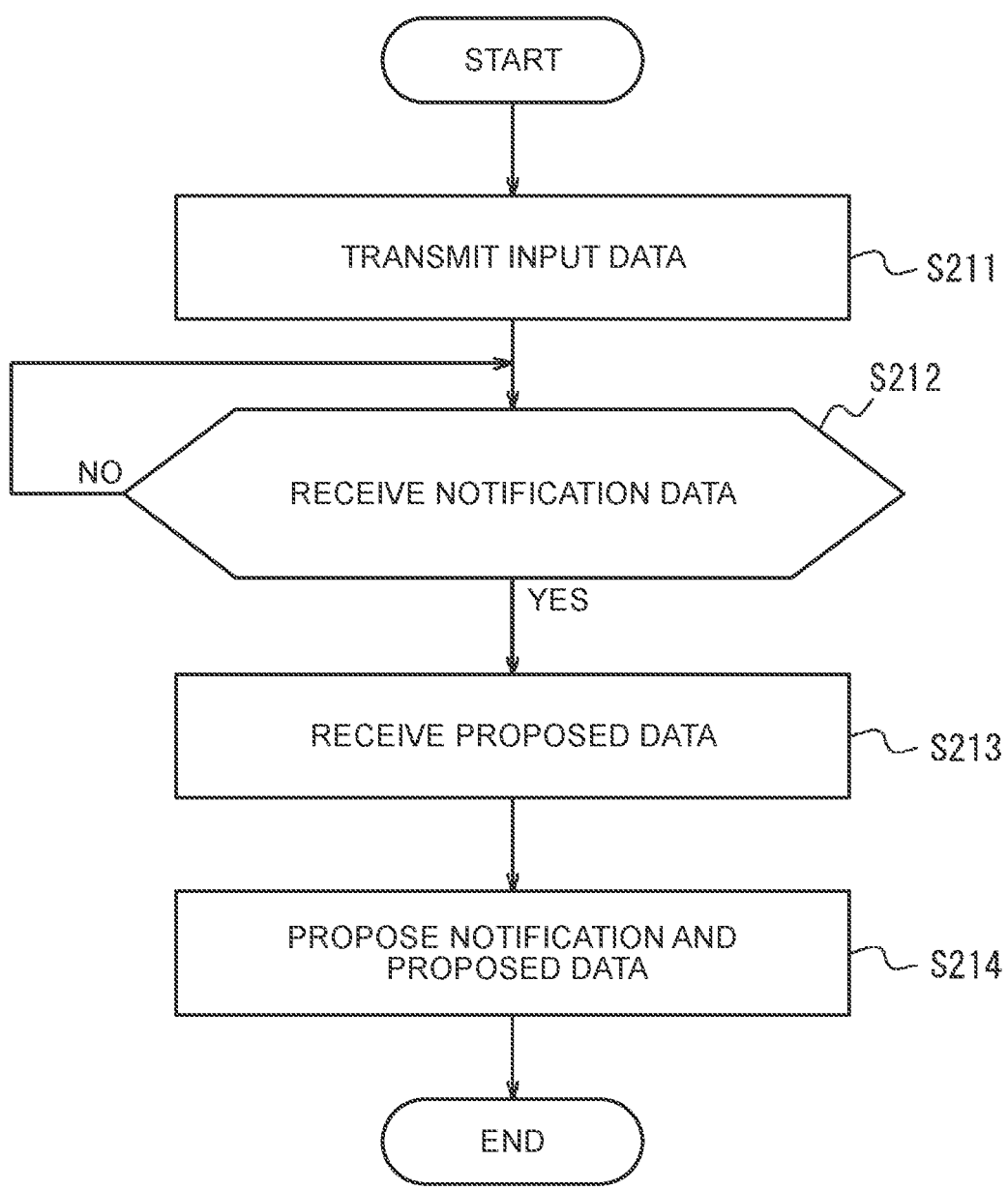

CONTROL DEVICE, SYSTEM, COMPUTER-READABLE MEDIUM, AND MATCHING METHOD

CROSS-REFERENCE TO RELATED APPLICATION

This application claims priority to Japanese Patent Application No. 2021-017772 filed on Feb. 5, 2021, incorporated herein by reference in its entirety.

BACKGROUND

1. Technical Field

The present disclosure relates to a control device, a system, a computer-readable medium, and a matching method.

2. Description of Related Art

Japanese Unexamined Patent Application Publication No. 2013-113070 (JP 2013-113070 A) discloses a building containing a vehicle provided with a container portion for a person to take shelter in the event of a disaster.

SUMMARY

Families who evacuate in vehicles tend to be stressed by being isolated from their surroundings.

An object of the present disclosure is to relieve the stress of family members staying in the vehicle.

A control device according to the present disclosure includes: a communication unit that receives input data from a terminal device of a first member who is a member of a first family staying in a vehicle, the input data indicating a family composition and a family stress for the first family; and a control unit that searches a database in which data indicating the family composition and the family stress for each of a plurality of families staying in individual vehicles is registered, using the input data received by the communication unit as a search key, selects a second family from the families based on a search result acquired, and causes the communication unit to transmit notification data that notifies the first member of information for establishing a relationship with a second member who is a member of the second family selected.

A computer-readable medium according to the present disclosure stores a program that causes a computer to perform operations including: transmitting input data to a control device, the input data indicating a family composition and a family stress for a first family staying in a vehicle and being input by a first member who is a member of the first family; receiving, when the control device searches a database in which data indicating the family composition and the family stress is registered for each of a plurality of families staying in individual vehicles using the transmitted input data as a search key and selects a second family among the families based on a search result obtained, notification data notifying the first member of information for establishing a relationship with a second member who is a member of the selected second family from the control device; prompting the first member to establish the relationship with the second member by presenting the received notification data.

A matching method according to the present disclosure includes: transmitting input data from a terminal device of a first member who is a member of a first family staying in a vehicle to a control device, the input data indicating a family composition and a family stress for the first family; searching a database in which data indicating the family composition and the family stress for each of a plurality of families staying in individual vehicles is registered, using the input data as a search key, selecting a second family from the families by the control device based on a search result obtained; transmitting notification data that notifies the first member of information for establishing a relationship with a second member who is a member of the second family selected, from the control device to a terminal device of the first member.

According to the present disclosure, the stress of the member of the family staying in the vehicle can be relieved.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 2 is a table showing an example of data registered in a database according to the embodiment of the first disclosure;

FIG. 8 is a flowchart showing an operation of a control device according to a second embodiment of the present disclosure; and FIG. 9 is a flowchart showing an operation of a first terminal device according to the second embodiment of the present disclosure.

DETAILED DESCRIPTION OF EMBODIMENTS

Figure 1:
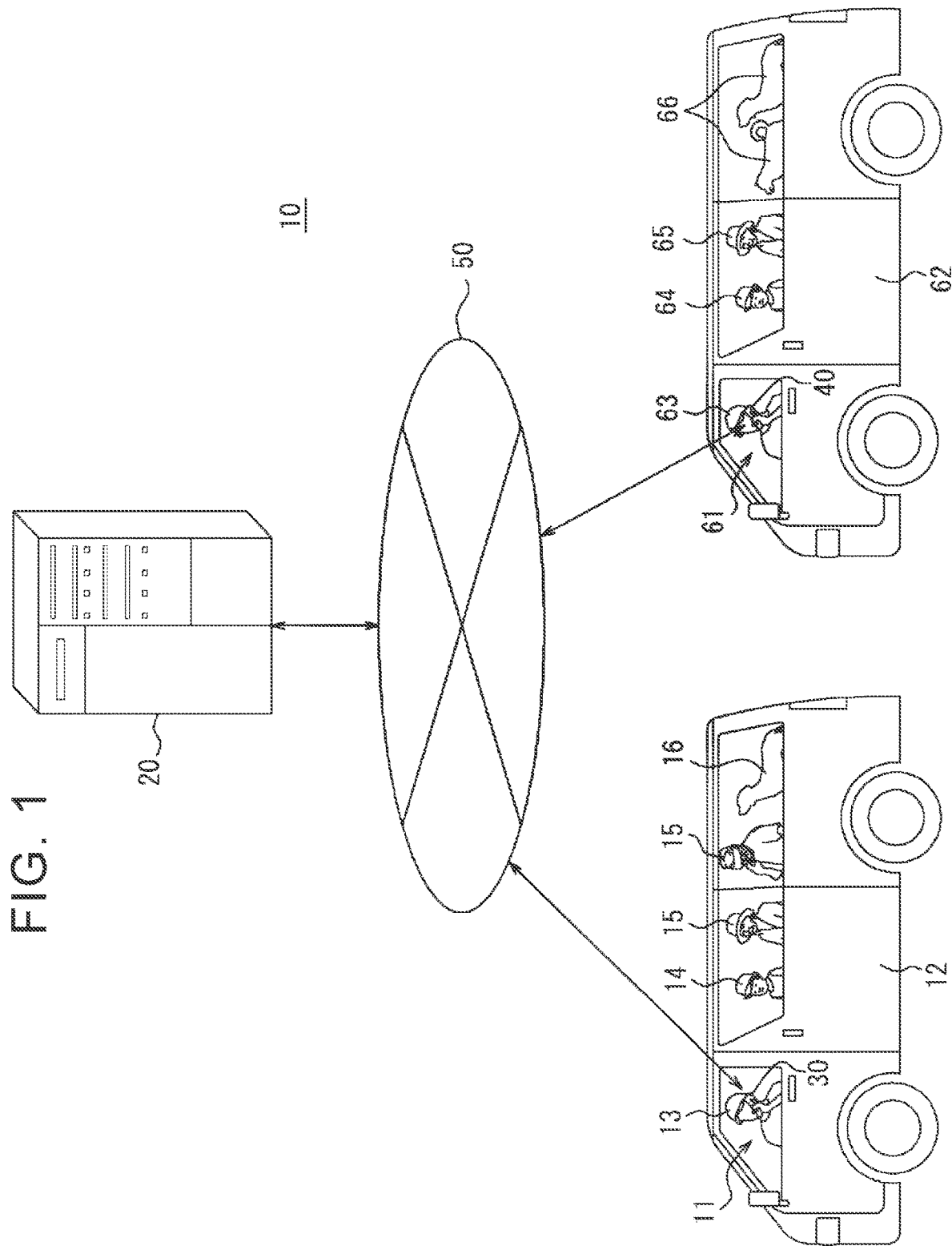
FIG. 1 is a diagram showing a configuration of a system according to an embodiment of a first disclosure.

Hereinafter, embodiments of the present disclosure will be described below with reference to the drawings.

In each drawing, the same or corresponding portions are denoted by the same reference signs. In the description of each embodiment, description of the same or corresponding components will be appropriately omitted or simplified.

A first embodiment that is an embodiment of the present disclosure will be described.

The configuration of a system 10 according to the present embodiment will be described with reference to FIG. 1.

The system 10 according to the present embodiment includes at least one control device 20 and two or more terminal devices such as a first terminal device 30 and a second terminal device 40. The control device 20 can communicate with the terminal devices via a network 50.

Each of the terminal devices can communicate with other terminal devices via the network 50.

The control device 20 is installed in facilities such as a data center. The control device 20 is, for example, a computer such as a server belonging to a cloud computing system or other computing systems.

Each of the terminal devices is, for example, a mobile device such as a mobile phone, a smartphone, or a tablet, or an in-vehicle device such as a car navigation device.

The network 50 includes the Internet, at least one WAN, at least one MAN, or any combination thereof. The term "WAN" is an abbreviation for "wide area network". The term "MAN" is an abbreviation for "metropolitan area network". The network 50 may include at least one wireless network, at least one optical network, or any combination thereof. The wireless network is, for example, an ad hoc network, a cellular network, a wireless LAN, a satellite communication network, or a terrestrial microwave network. The term "LAN" is an abbreviation for "local area network".

The outline of the present embodiment will be described with reference to FIGS. 1 and 2.

The first terminal device 30 is a terminal device of a first member 13. The first member 13 is a member of a first family 11 who stays in a vehicle 12. The first terminal device 30 transmits input data D1 to the control device 20. The input data D1 is data indicating a family composition a family stress for the first family 11.

The control device 20 receives the input data D1 from the first terminal device 30. The control device 20 searches a database 27 using the received input data D1 as a search key. In the database 27, data indicating the family composition and the family stress is registered as registration data D2 for each of a plurality of families staying in individual vehicles. The control device 20 selects a second family 61 from the families based on the obtained search results. In the present embodiment, the second family 61 is at least one family that has something in common with the first family 11 in both the family composition and the family stress indicated by the data registered in the database 27. The control device 20 transmits notification data D3 to the first terminal device 30. The notification data D3 is data for notifying the first member 13 of information for establishing a relationship with the second member 63. The second member 63 is a member of the second family 61 selected by the control device 20.

The first terminal device 30 receives the notification data D3 from the control device 20. The first terminal device 30 prompts the first member 13 to establish a relationship with the second member 63 by presenting the received notification data D3. The first member 13 can avoid isolation by establishing some relationship with the second member 63. Therefore, according to the present embodiment, the stress of the first member 13 can be relieved.

In the present embodiment, the input data D1 includes data indicating whether the first family 11 has a child. The input data D1 further includes data indicating whether the first member 13 is under stress due to childcare or illness of the child. The registration data D2 includes data indicating whether each family has a child. The registration data D2 further includes data indicating whether the members of each family are under stress due to childcare or illness of the child. For example, the registration data D2 includes data indicating whether the second family 61 has a child. The registration data D2 further includes data indicating whether the second member 63 is under stress due to childcare or illness of the child.

In the present embodiment, the input data D1 includes data indicating whether the first family 11 has an elderly person. The input data D1 further includes data indicating whether the first member 13 is under stress due to elderly care or illness of the elderly person. The registration data D2 includes data indicating whether each family has an elderly person. The registration data D2 further includes data indicating whether the members of each family are under stress due to elderly care or illness of the elderly person. For example, the registration data D2 includes data indicating whether the second family 61 has an elderly person. The registration data D2 further includes data indicating whether the second member 63 is under stress due to elderly care or illness of the elderly person.

In the present embodiment, the input data D1 includes data indicating whether the first family 11 has a pet. The input data D1 further includes data indicating whether the first member 13 is under stress due to pet care or illness of the pet. The registration data D2 includes data indicating whether each family has a pet. The registration data D2 further includes data indicating whether the members of each family are under stress due to pet care or illness of the pet. For example, the registration data D2 includes data indicating whether the second family 61 has a pet. The registration data D2 further includes data indicating whether the second member 63 is under stress due to pet care or illness of the pet.

In the example shown in FIG. 1, the first family 11 has one child 14, two elderly persons 15, and one pet 16. The first member 13 is a parent of the child 14, a child of the elderly persons 15, and an owner of the pet 16. It is assumed that the first member 13 is under stress due to childcare, elderly care, illness of the elderly persons 15, and care of the pet 16.

In the present embodiment, when the control device 20 receives the input data D1, the received input data D1 is registered in the database 27 as a part of the registration data D2. Therefore, in the example shown in FIG. 2, for the first family 11, the data indicating the family composition and the family stress above are registered in the database 27 in association with a family ID "1" of the first family 11.

In the example shown in FIG. 1, the second family 61 has one child 64, one elderly person 65, and two pets 66. The second member 63 is a parent of the child 64, a child of the elderly person 65, and an owner of the pets 66. It is assumed that the second member 63 is under stress due to childcare, elderly care, care of the pets 66, and illness of the pets 66.

In the example shown in FIG. 2, for the second family 61, the data indicating the family composition and the family stress above are registered in the database 27 in association with the family ID "2" of the second family 61. That is, the second family 61 has similarities with the first family 11 in the family composition indicated by the registration data D2 in that both families have a child, an elderly person, and a pet. The second family 61 also has similarities with the first family 11 in terms of the family stress indicated by the registration data D2 in that the member is under stress due to childcare, elderly care, and pet care.

In the present embodiment, the notification data D3 is data for notifying the first member 13 of contact information for communicating with the second member 63. Specifically, the notification data D3 is data for notifying the first member 13 of the telephone number, e-mail address, messaging application ID, or any combination thereof of the second terminal device 40 as the contact information. The term "ID" is an abbreviation for identifier. The second terminal device 40 is a terminal device of the second member 63. The first terminal device 30 urges the first member 13 to establish a friendship with the second member 63 by presenting the notification data D3. The first member 13 can avoid isolation by establishing friendship with the second member 63. In the example shown in FIG. 2, the first member 13 can relieve stress by consulting with the second member 63 regarding childcare, elderly care, or pet care.

As a modification of the present embodiment, the notification data D3 may be data that notifies the first member 13 of position information indicating a parking position of the vehicle 12 of the first family 11 so as to park the vehicle 12 near a vehicle 62 of the second family 61. Specifically, the notification data D3 may be data that notifies the first member 13 of coordinates or an address of an available parking position around the parking position of the vehicle 62 of the second family 61, or coordinates of a parking lot where the vehicle 62 of the second family 61 is parked as the position information. The first terminal device 30 may urge the first member 13 to establish a neighbor relationship with the second member 63 by presenting the notification data D3. In that case, the first member 13 can avoid isolation by establishing the neighbor relationship with the second member 63. In the example shown in FIG. 2, the first member 13 can relieve the stress by seeing that the second member 63 also takes care of the child, the elderly person, or the pet.

Figure 3:
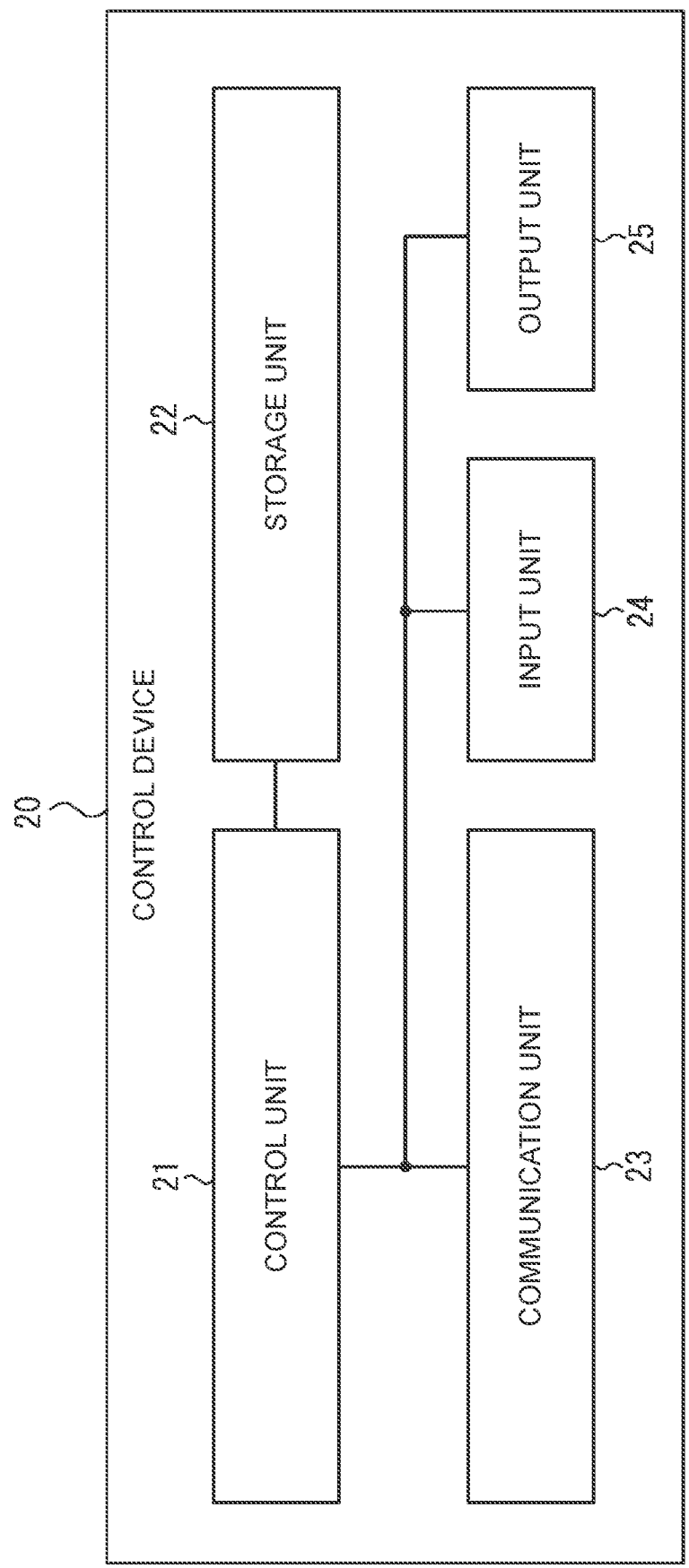
FIG. 3 is a block diagram showing a configuration of a control device according to the embodiment of the first disclosure.

The configuration of the control device 20 according to the present embodiment will be described with reference to FIG. 3.

The control device 20 includes a control unit 21, a storage unit 22, a communication unit 23, an input unit 24, and an output unit 25.

The control unit 21 includes at least one processor, at least one programmable circuit, at least one dedicated circuit, or any combination thereof. The processor is a general-purpose processor such as a CPU or GPU, or a dedicated processor specialized for a specific process. The term "CPU" is an abbreviation for "central processing unit". The term "GPU" is an abbreviation for "graphics processing unit". The programmable circuit is, for example, an FPGA. The term "FPGA" is an abbreviation for "field-programmable gate array". The dedicated circuit is, for example, an ASIC. The term "ASIC" is an abbreviation for "application specific integrated circuit". The control unit 21 executes processes related to an operation of the control device 20 while controlling each unit of the control device 20.

The storage unit 22 includes at least one semiconductor memory, at least one magnetic memory, at least one optical memory, or any combination thereof. The semiconductor memory is, for example, a RAM or a ROM. The term "RAM" is an abbreviation for "random access memory". The term "ROM" is an abbreviation for "read-only memory". The RAM is, for example, an SRAM or a DRAM. The term "SRAM" is an abbreviation for "static random access memory". The term "DRAM" is an abbreviation for "dynamic random access memory". The ROM is, for example, an EEPROM. The term "EEPROM" is an abbreviation for "electrically erasable programmable read-only memory". The storage unit 22 functions as, for example, a main storage device, an auxiliary storage device, or a cache memory. The storage unit 22 stores data used for the operation of the control device 20 and data acquired through the operation of the control device 20. Although the database 27 is built in the storage unit 22 in the present embodiment, the database 27 may be built in an external storage and connected to the control device 20.

The communication unit 23 includes at least one communication interface. The communication interface is, for example, a LAN interface. The communication unit 23 receives the data used for the operation of the control device 20, and transmits the data acquired through the operation of the control device 20.

The input unit 24 includes at least one input interface. The input interface is, for example, a physical key, a capacitive key, a pointing device, a touch screen integrated with a display, a camera, or a microphone. The input unit 24 accepts an operation of inputting data used for the operation of the control device 20. The input unit 24 may be connected to the control device 20 as an external input device instead of being provided in the control device 20. As the connection interface, for example, an interface corresponding to a standard such as USB, HDMI (registered trademark), or Bluetooth (registered trademark) can be used. The term "USB" is an abbreviation for "universal serial bus". The term "HDMI (registered trademark)" is an abbreviation for "high-definition multimedia interface".

The output unit 25 includes at least one output interface. The output interface is, for example, a display or a speaker. The display is, for example, an LCD or an organic EL display. The term "LCD" is an abbreviation for "liquid crystal display". The term "EL" is an abbreviation for "electroluminescence". The output unit 25 outputs the data acquired through the operation of the control device 20. The output unit 25 may be connected to the control device 20 as an external output device instead of being provided in the control device 20. As the connection interface, for example, an interface corresponding to a standard such as USB, HDMI (registered trademark), or Bluetooth (registered trademark) can be used.

The function of the control device 20 is realized by executing a control program according to the present embodiment with the processor serving as the control unit 21. That is, the function of the control device 20 is realized by software. The control program causes the computer to perform the operation of the control device 20 such that the computer functions as the control device 20. That is, the computer functions as the control device 20 by performing the operation of the control device 20 in accordance with the control program.

The program can be stored in a non-transitory computer-readable medium. The non-transitory computer-readable medium is, for example, a flash memory, a magnetic recording device, an optical disc, an opto-magnetic recording medium, or a ROM. The distribution of the program is carried out, for example, by selling, transferring, or renting a portable medium such as am SD card, a DVD, or a CD-ROM in which the program is stored. The term "SD" is an abbreviation for "secure digital". The term "DVD" is an abbreviation for "digital versatile disc". The term "CD-ROM" is an abbreviation for "compact disc read-only memory". The program may be stored in the storage of the server and transferred from the server to other computers to distribute the program. The program may be provided as a program product.

The computer temporarily stores the program stored in the portable medium or the program transferred from the server in the main storage device, for example. Then, the computer causes the processor to read the program stored in the main storage device, and causes the processor to perform processes according to the read program. The computer may read the program directly from the portable medium and perform processes according to the program. The computer may perform the processes according to the received program each time the program is transferred from the server to the computer. The processes may be executed by a so-called ASP service that realizes the function only by execution instruction and result acquisition without transferring the program from the server to the computer. The term "ASP" is an abbreviation for "application service provider". The program includes information that is used for processing by electronic computers and equivalent to a program. For example, data that is not a direct command to a computer but has the property of defining the processing of the computer corresponds to the "data equivalent to a program".

A part or all of the functions of the control device 20 may be realized by a programmable circuit or a dedicated circuit as the control unit 21. That is, a part or all of the functions of the control device 20 may be realized by hardware.

Figure 4:
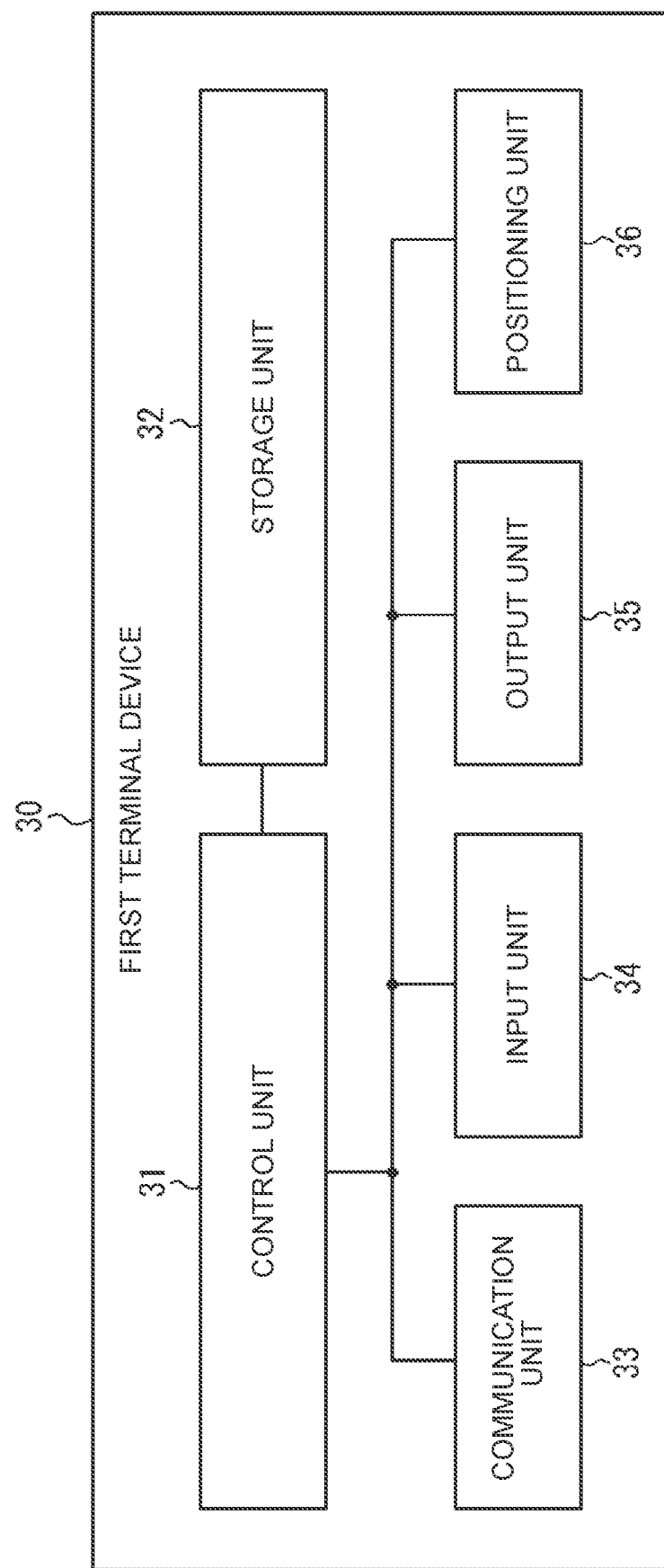
FIG. 4 is a block diagram showing a configuration of a first terminal device according to the first embodiment of the present disclosure.

The configuration of the first terminal device 30 according to the present embodiment will be described with reference to FIG. 4.

The first terminal device 30 includes a control unit 31, a storage unit 32, a communication unit 33, an input unit 34, an output unit 35, and a positioning unit 36.

The control unit 31 includes at least one processor, at least one programmable circuit, at least one dedicated circuit, or any combination thereof. The processor is a general-purpose processor such as a CPU or GPU, or a dedicated processor specialized for a specific process. The programmable circuit is, for example, an FPGA. The dedicated circuit is, for example, an ASIC. The control unit 31 executes the processes related to the operation of the first terminal device 30 while controlling each unit of the first terminal device 30.

The storage unit 32 includes at least one semiconductor memory, at least one magnetic memory, at least one optical memory, or any combination thereof. The semiconductor memory is, for example, a RAM or a ROM. The RAM is, for example, an SRAM or a DRAM. The ROM is, for example, an EEPROM. The storage unit 32 functions as, for example, a main storage device, an auxiliary storage device, or a cache memory. The storage unit 32 stores data used for the operation of the first terminal device 30 and data acquired through the operation of the first terminal device 30.

The communication unit 33 includes at least one communication interface. The communication interface is, for example, an interface compatible with mobile communication standards such as LTE, 4G standard, or 5G standard, an interface compatible with short-range wireless communication standard such as Bluetooth (registered trademark), or a LAN interface. The term "LTE" is an abbreviation for "long term evolution". The term "4G" is an abbreviation for "fourth generation". The term "5G" is an abbreviation for "fifth generation". The communication unit 33 receives the data used for the operation of the first terminal device 30, and transmits the data acquired through the operation of the first terminal device 30.

The input unit 34 includes at least one input interface. The input interface is, for example, a physical key, a capacitive key, a pointing device, a touch screen integrated with a display, a camera, or a microphone. The input unit 34 accepts an operation of inputting data used for the operation of the first terminal device 30. The input unit 34 may be connected to the first terminal device 30 as an external input device instead of being provided in the first terminal device 30. As the connection interface, for example, an interface corresponding to a standard such as USB, HDMI (registered trademark), or Bluetooth (registered trademark) can be used.

The output unit 35 includes at least one output interface. The output interface is, for example, a display or a speaker. The display is, for example, a LCD or an organic EL display. The output unit 35 outputs the data acquired through the operation of the first terminal device 30. The output unit 35 may be connected to the first terminal device 30 as an external output device instead of being provided in the first terminal device 30. As the connection interface, for example, an interface corresponding to a standard such as USB, HDMI (registered trademark), or Bluetooth (registered trademark) can be used.

The positioning unit 36 includes at least one GNSS receiver. The term "GNSS" is an abbreviation for "global navigation satellite system". The GNSS is, for example, GPS, QZSS, BDS, GLONASS, or Galileo. The term "GPS" is an abbreviation for "global positioning system". The term "QZSS" is an abbreviation for "quasi-zenith satellite system". The satellites of the QZSS are referred to as quasi-zenith satellites. The term "BDS" is an abbreviation for "BeiDou navigation satellite system". The term "GLONASS" is an abbreviation for "global navigation satellite system". The positioning unit 36 measures the position of the first terminal device 30.

The function of the first terminal device 30 is realized by executing the terminal program according to the present embodiment with the processor corresponding to the control unit 31. That is, the function of the first terminal device 30 is realized by software. The terminal program causes the computer to perform the operation of the first terminal device 30 such that the computer functions as the first terminal device 30. That is, the computer functions as the first terminal device 30 by performing the operation of the first terminal device 30 according to the terminal program.

A part or all of the functions of the first terminal device 30 may be realized by a programmable circuit or a dedicated circuit as the control unit 31. That is, a part or all of the functions of the first terminal device 30 may be realized by hardware.

Figure 5:
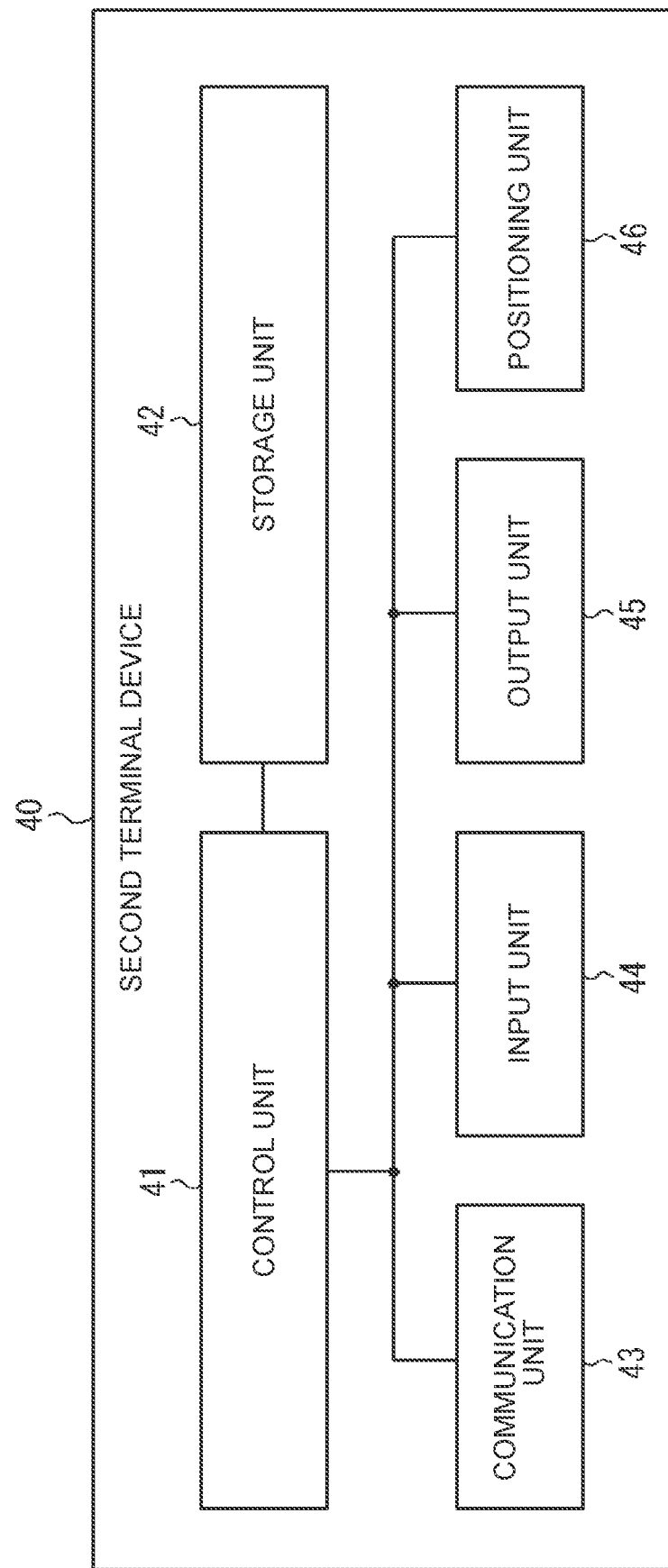
FIG. 5 is a block diagram showing a configuration of a second terminal device according to the first embodiment of the present disclosure.

The configuration of the second terminal device 40 according to the present embodiment will be described with reference to FIG. 5.

The second terminal device 40 includes a control unit 41, a storage unit 42, a communication unit 43, an input unit 44, an output unit 45, and a positioning unit 46.

The control unit 41 includes at least one processor, at least one programmable circuit, at least one dedicated circuit, or any combination thereof. The processor is a general-purpose processor such as a CPU or GPU, or a dedicated processor specialized for a specific process. The programmable circuit is, for example, an FPGA. The dedicated circuit is, for example, an ASIC. The control unit 41 executes the processes related to the operation of the second terminal device 40 while controlling each unit of the second terminal device 40.

The storage unit 42 includes at least one semiconductor memory, at least one magnetic memory, at least one optical memory, or any combination thereof. The semiconductor memory is, for example, a RAM or a ROM. The RAM is, for example, an SRAM or a DRAM. The ROM is, for example, an EEPROM. The storage unit 42 functions as, for example, a main storage device, an auxiliary storage device, or a cache memory. The storage unit 42 stores data used for the operation of the second terminal device 40 and data acquired through the operation of the second terminal device 40.

The communication unit 43 includes at least one communication interface. The communication interface is, for example, an interface compatible with mobile communication standards such as LTE, the 4G standard, or the 5G standard, an interface compatible with short-range wireless communication standard such as Bluetooth (registered trademark), or a LAN interface. The communication unit 43 receives the data used for the operation of the second terminal device 40, and transmits the data acquired through the operation of the second terminal device 40.

The input unit 44 includes at least one input interface. The input interface is, for example, a physical key, a capacitive key, a pointing device, a touch screen integrated with a display, a camera, or a microphone. The input unit 44 accepts an operation of inputting data used for the operation of the second terminal device 40. The input unit 44 may be connected to the second terminal device 40 as an external input device instead of being provided in the second terminal device 40. As the connection interface, for example, an interface corresponding to a standard such as universal serial bus (USB), high-definition multimedia interface (HDMI; registered trademark), or Bluetooth (registered trademark) can be used.

The output unit 45 includes at least one output interface. The output interface is, for example, a display or a speaker. The display is, for example, a LCD or an organic EL display. The output unit 45 outputs the data acquired through the operation of the second terminal device 40. The output unit 45 may be connected to the second terminal device 40 as an external output device instead of being provided in the second terminal device 40. As the connection interface, for example, an interface corresponding to a standard such as USB, HDMI (registered trademark), or Bluetooth (registered trademark) can be used.

The positioning unit 46 includes at least one GNSS receiver. The GNSS is, for example, GPS, QZSS, BDS, GLONASS, or Galileo. The positioning unit 46 measures the position of the second terminal device 40.

The function of the second terminal device 40 is realized by executing the terminal program according to the present embodiment with the processor corresponding to the control unit 41. That is, the function of the second terminal device 40 is realized by software. The terminal program causes the computer to perform the operation of the second terminal device 40 such that the computer functions as the second terminal device 40. That is, the computer functions as the second terminal device 40 by performing the operation of the second terminal device 40 according to the terminal program.

A part or all of the functions of the second terminal device 40 may be realized by a programmable circuit or a dedicated circuit as the control unit 41. That is, a part or all of the functions of the second terminal device 40 may be realized by hardware.

Figure 6:
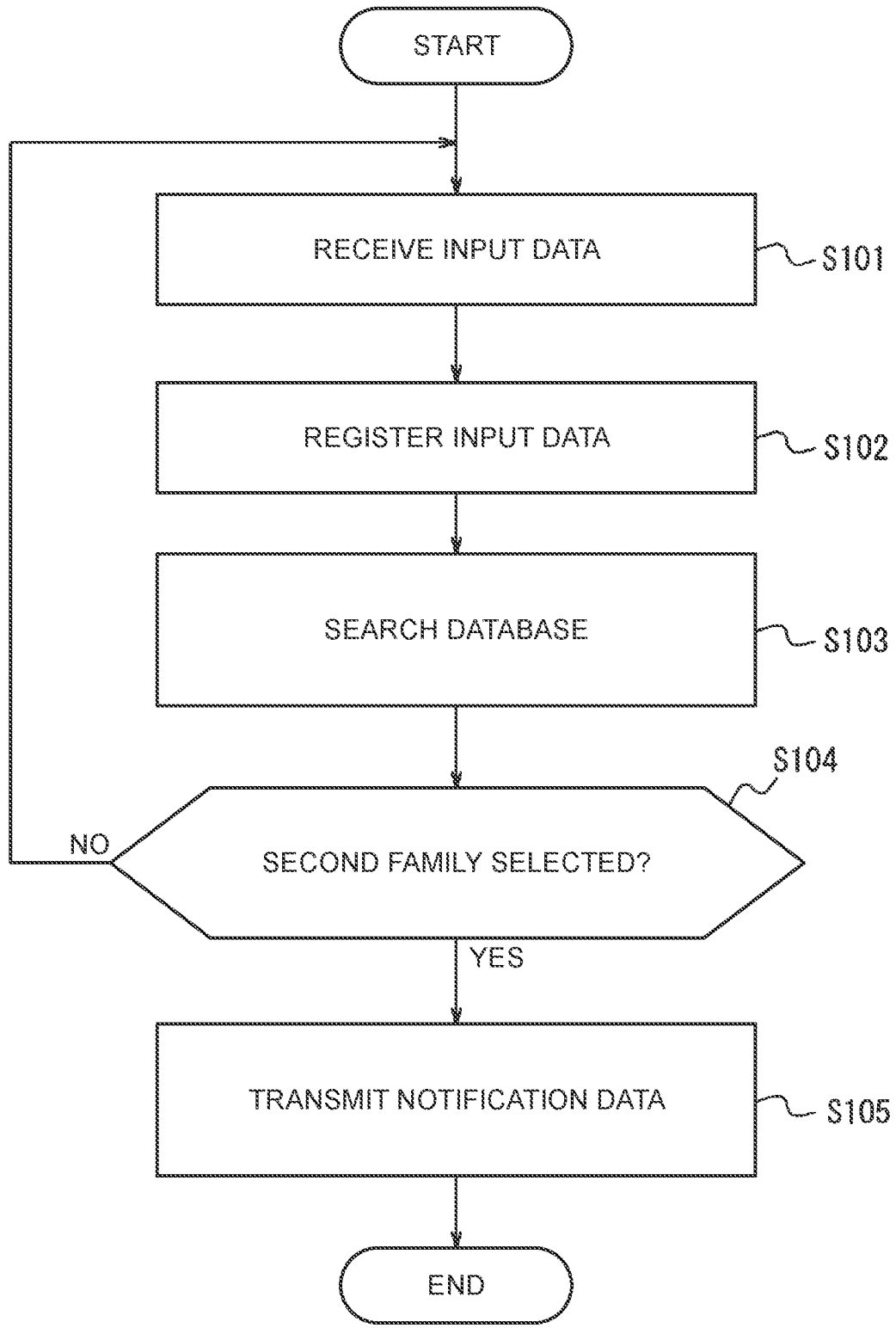
FIG. 6 is a flowchart showing an operation of a control device according to the first embodiment of the present disclosure.
Figure 7:
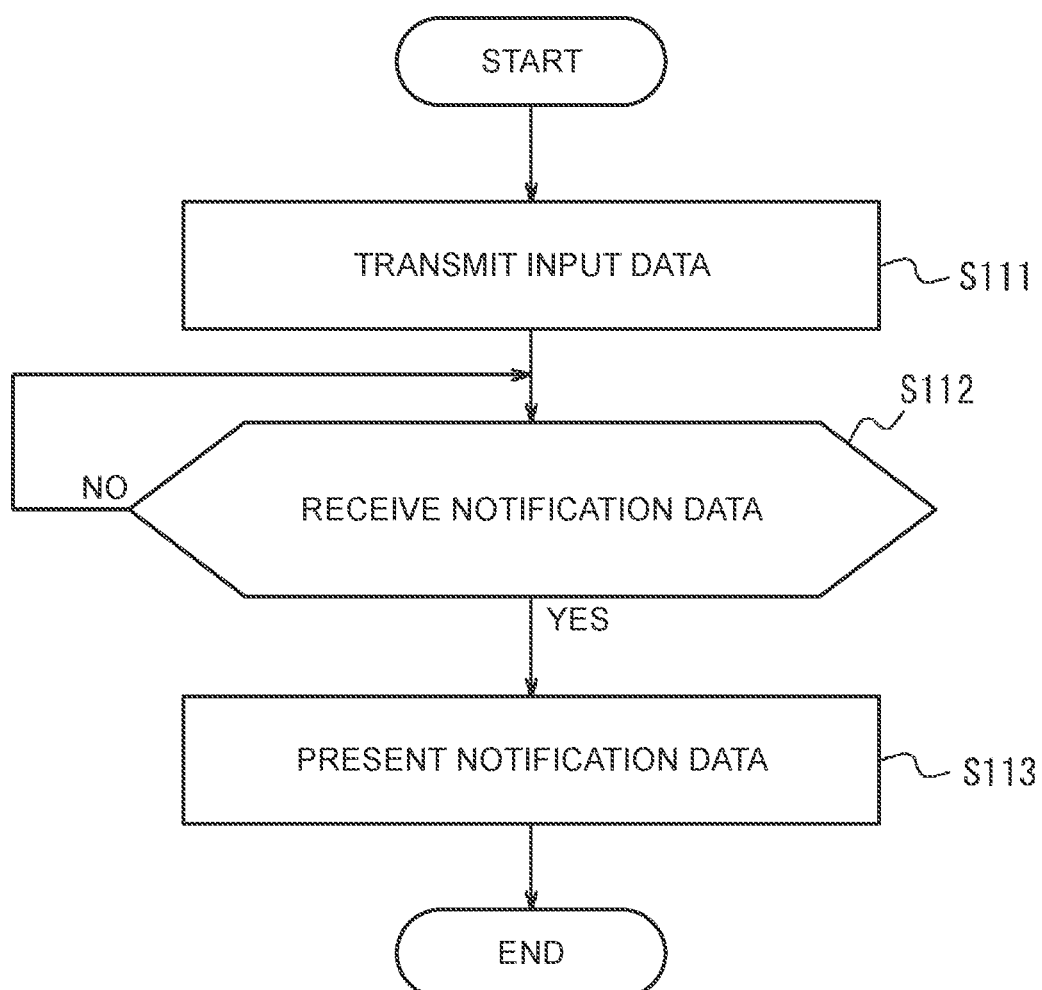
FIG. 7 is a flowchart showing an operation of the first terminal device according to the first embodiment of the present disclosure.

The configuration of a system 10 according to the present embodiment will be described with reference to FIG. 6 and FIG. 7. The operation corresponds to the proposition method according to the present embodiment. FIG. 6 shows the operation of the control device 20. FIG. 7 shows the operation of the first terminal device 30.

In step S111 in FIG. 7, the control unit 31 of the first terminal device 30 first receives, from the first member 13, an operation of inputting the family composition and the family stress for the first family 11 staying in the vehicle 12 via the input unit 34. The control unit 31 may ask a question about the family composition and the family stress through the speaker as the output unit 35, and may receive an answer from the first member 13 via the microphone as the input unit 34. The control unit 31 causes the communication unit 33 to transmit the input data D1. The input data D1 is data indicating the family composition and the family stress input by the first member 13. The communication unit 33 transmits the input data D1 to the control device 20.

In step S101 in FIG. 6, the communication unit 23 of the control device 20 receives the input data D1 transmitted in step S111 in FIG. 7 from the first terminal device 30. The control unit 21 of the control device 20 acquires the input data D1 received by the communication unit 23.

In step S102 in FIG. 6, the control unit 21 of the control device 20 registers the input data D1 acquired in step S101 to the database 27. In the example shown in FIG. 2, the control unit 21 adds a record indicating a new family ID "1", a family composition "one child, two elderly persons, and one pet", and the family stress "childcare, elderly care, illness of the elderly persons, and pet care" to the table of database 27.

In step S103 in FIG. 6, the control unit 21 of the control device 20 searches the database 27 using the input data D1 acquired in step S101 as a search key. In the example shown in FIG. 2, the control unit 21 searches the table of the database 27 using the family composition "child, the elderly person, or pet" and the family stress "childcare, elderly care, illness of the elderly person, or pet care" as search keys.

In step S104 in FIG. 6, the control unit 21 of the control device 20 selects the second family 61 from the families based on the search result obtained in step S103. Specifically, the control unit 21 selects, as the second family 61, at least one family that has something in common with the first family 11 in both the family composition and the family stress indicated by the registration data D2. The registration data D2 is the data registered in the database 27. The registration data D2 is data indicating the family composition and the family stress for each of the families staying in individual vehicles. In the example shown in FIG. 2, the control unit 21 extracts a record indicating the family ID "2", the family composition "one child, one elderly person, and two pets", and the family stress "childcare, elderly care, pet care, and illness of the pet" from the table of database 27. When the number of search results is 0, that is, there is no selectable family, the processes after step S101 are executed again.

In step S105 in FIG. 6, the control unit 21 of the control device 20 causes the communication unit 23 to transmit the notification data D3. The notification data D3 is data for notifying the first member 13 of information for establishing a relationship with the second member 63 who is a member of the second family 61 selected in step S104. The communication unit 23 transmits the notification data D3 to the first terminal device 30. Specifically, the communication unit 23 transmits data for notifying the first member 13 of contact information for communicating with the second member 63 to the first terminal device 30 as the notification data D3.

After step S111 in FIG. 7, the first terminal device 30 is on standby until the second family 61 is selected by the control device 20. When the second family 61 is selected by the control device 20, in step S112, the communication unit 33 of the first terminal device 30 receives the notification data D3 transmitted in step S105 in FIG. 6 from the control device 20. The control unit 31 of the first terminal device 30 acquires the notification data D3 received by the communication unit 33.

In step S113 in FIG. 7, the control unit 31 of the first terminal device 30 prompts the first member 13 to establish a relationship with the second member 63 by presenting the notification data D3 acquired in step S112. Specifically, the control unit 31 displays the contact information included in the notification data D3 on the display as the output unit 35. Alternatively, the control unit 31 outputs the contact information included in the notification data D3 by voice from the speaker serving as the output unit 35.

The second terminal device 40 may perform the same operation as that shown in FIG. 7 before the first terminal device 30. For example, similar to step S111 in FIG. 7, the control unit 41 of the second terminal device 40 may receive, from the second member 63, an operation of inputting the family composition and the family stress for the second family 61 staying in the vehicle 62 via the input unit 44. The communication unit 43 of the second terminal device 40 may transmit the input data D4 to the control device 20. The input data D4 is data indicating the family composition and the family stress input by the second member 63. In step S101 in FIG. 6, the communication unit 23 of the control device 20 may receive the input data D4 from the second terminal device 40. In step S102 in FIG. 6, the control unit 21 of the control device 20 may register the input data D4 received by the communication unit 23 in the database 27. In the example shown in FIG. 2, the control unit 21 may add a record indicating the family ID "2", the family composition "one child, one elderly person, and two pets", and the family stress "childcare, elderly care, pet care, and illness of the pet" to the table of database 27.

In step S105 in FIG. 6, the communication unit 23 of the control device 20 may transmit the notification data D5 to the second terminal device 40. The notification data D5 is data for notifying the second member 63 of the contact information for communicating with the first member 13. For example, when the second family 61 is selected by the control device 20, similar to step S112 in FIG. 7, the communication unit 43 of the second terminal device 40 receives the notification data D5 transmitted in step S105 in FIG. 6 from the control device 20. Similar to step S113 in FIG. 7, the control unit 41 of the second terminal device 40 prompts the first member 13 to establish a relationship with the second member 63 by presenting the notification data D5 received from the communication unit 43.

As described above, in the present embodiment, the control unit 21 of the control device 20 acquires information about the stress felt by the person staying in the vehicle 12 due to reasons such as evacuation in the event of a disaster. The control unit 21 brings together those who are staying in the vehicle for the same reason and who are under the same stress. As a result, people with similar circumstances can communicate with each other to relieve stress.

As a modification of the present embodiment, a method of relieving the family stress common to the first family 11 and the second family 61 may be proposed. A second embodiment that is such a modification will be described.

The configuration of a system 10 according to the present embodiment will be described with reference to FIG. 8 and FIG. 9. The operation corresponds to the matching method according to the present embodiment. FIG. 8 shows the operation of the control device 20. FIG. 9 shows the operation of the first terminal device 30.

The processes in steps S201 to S205 in FIG. 8 and steps S211 and S212 in FIG. 9 are the same as the processes in steps S101 to S105 in FIG. 6, and steps S111 and S112 in FIG. 7, respectively. Therefore, the description thereof will be omitted.

In step S206 after step S205 in FIG. 8, the control unit 21 of the control device 20 causes the communication unit 23 to transmit proposal data D6. The proposal data D6 is data that proposes a method for alleviating the family stress common to the first family 11 and the second family 61. The method proposed in the proposal data D6 is, for example, conversation, meals, sports, games, or karaoke. The communication unit 23 transmits the proposal data D6 to the first terminal device 30.

In step S213 in FIG. 9, the communication unit 33 of the first terminal device 30 receives the proposal data D6 transmitted in step S206 in FIG. 8 from the control device 20. The control unit 31 of the first terminal device 30 acquires the proposal data D6 received by the communication unit 33.

In step S214 of FIG. 9, the control unit 31 of the first terminal device 30 presents the proposal data D6 acquired in step S213 in addition to the notification data D3 acquired in step S212 so as to prompt the first member 13 to positively relieve stress. Specifically, the control unit 31 displays a message explaining the method proposed in the proposal data D6 on the display as the output unit 35. Alternatively, the control unit 31 outputs the message explaining the method proposed in the proposal data D6 by voice from the speaker serving as the output unit 35.

In step S206 in FIG. 8, the communication unit 23 of the control device 20 may transmit the proposal data D6 to the second terminal device 40. For example, similar to step S213 in FIG. 9, the communication unit 43 of the second terminal device 40 may receive the proposal data D6 transmitted in step S206 in FIG. 8 from the control device 20. Similar to step S214 in FIG. 9, the control unit 41 of the second terminal device 40 prompts the second member 63 to positively relieve stress by presenting the proposal data D6 received from the communication unit 43.

As described above, in the present embodiment, the control unit 21 of the control device 20 can propose a stress relieving method suitable for people in similar circumstances. For example, when karaoke is proposed as a stress relieving method, the vehicle of each family may be used as a karaoke box, and a singing contest between families may be held using vehicle-to-vehicle communication. In that case, a noise canceling function may be implemented in the vehicle of each family in order to avoid troubles caused by noise. Alternatively, the parking area may be allocated separately for the vehicle used as a karaoke box and other vehicles. In such a modification, the communication unit 23 of the control device 20 transmits notification data D7 to a terminal device of a third member. The notification data D7 is data for notifying the parking position of the vehicle of a third family for parking away from the vehicle 12 of the first family 11 and the vehicle 62 of the second family 61. The third family is at least one family other than the second family 61 among the families. The third member is a member of the third family. The terminal device of the third member receives the notification data D7 transmitted from the control device 20. The terminal device of the third member prompts the third member to park away from the vehicle 12 of the first family 11 and the vehicle 62 of the second family 61 by presenting the received notification data D7. As a further modification, when the method involves generation of noise although the method proposed in the proposal data D6 is not karaoke, the communication unit 23 of the control device 20 may transmit the notification data D7 to the terminal device of the third member.

The present disclosure is not limited to the embodiments described above. For example, two or more blocks shown in the block diagram may be integrated, or a single block may be divided. Instead of executing two or more steps shown in the flowcharts in chronological order according to the description, the steps may be executed in parallel or in a different order, depending on the processing capacities of the devices that execute the steps, or as necessary. Other changes may be made without departing from the scope of the present disclosure.

What is claimed is:

1. A control device, comprising:
   a communication unit that receives input data from a terminal device of a first member who is a member of a first family staying in a vehicle, the input data indicating a family composition and a family stress for the first family; and
   a control unit that searches a database in which data indicating the family composition and the family stress for each of a plurality of families staying in individual vehicles is registered, using the input data received by the communication unit as a search key, selects a second family from the families based on a search result acquired, and causes the communication unit to transmit notification data that notifies the first member of information for establishing a relationship with a second member who is a member of the second family selected.

2. The control device according to claim 1, wherein the control unit selects, as the second family, at least one family that has something in common with the first family in both the family composition and the family stress indicated by the data registered in the database.

3. The control device according to claim 1, wherein the communication unit transmits, as the notification data, data for notifying the first member of contact information for communicating with the second member to a terminal device of the first member.

4. The control device according to claim 1, wherein the communication unit transmits, as the notification data, data for notifying the first member of position information indicating a parking position of the vehicle of the first family so as to park the vehicle of the first family near the vehicle of the second family to a terminal device of the first member.

5. The control device according to claim 4, wherein the control unit further causes the communication unit to transmit proposal data proposing a method for relieving the family stress in common with the first family and the second family.

6. The control device according to claim 5, wherein the communication unit transmits data to a terminal device of a third member who is a member of a third family when the method proposed in the proposal data involves generation of noise, the data notifying a parking position of a vehicle of the third family that is at least one family other than the second family among the families so as to park the vehicle of the third family away from the vehicle of the first family and the vehicle of the second family.

7. The control device according to claim 1, wherein the data registered in the database includes data indicating whether each of the families has a child.

8. The control device according to claim 7, wherein the data registered in the database includes data indicating whether a member of each of the families is under stress due to childcare or illness of the child.

9. The control device according to claim 1, wherein the data registered in the database includes data indicating whether each of the families has an elderly person.

10. The control device according to claim 9, wherein the data registered in the database includes data indicating whether a member of each of the families is under stress due to elderly care or illness of the elderly person.

11. The control device according to claim 1, wherein the data registered in the database includes data indicating whether each of the families has a pet.

12. The control device according to claim 11, wherein the data registered in the database includes data indicating whether a member of each of the families is under stress due to pet care or illness of the pet.

13. A system, comprising:
    the control device according to claim 1; and
    a terminal device of the first member.

14. A non-transitory computer-readable medium storing a program that causes a computer to perform operations comprising:
    transmitting input data to a control device, the input data indicating a family composition and a family stress for a first family staying in a vehicle and being input by a first member who is a member of the first family;
    receiving, when the control device searches a database in which data indicating the family composition and the family stress is registered for each of a plurality of families staying in individual vehicles using the transmitted input data as a search key and selects a second family among the families based on a search result obtained, notification data notifying the first member of information for establishing a relationship with a second member who is a member of the selected second family from the control device; and
    prompting the first member to establish the relationship with the second member by presenting the received notification data.

15. The non-transitory computer-readable medium according to claim 14, wherein the notification data is data for notifying the first member of contact information for communicating with the second member.

16. The non-transitory computer-readable medium according to claim 14, wherein the notification data is data for notifying the first member of position information indicating a parking position of the vehicle of the first family so as to park the vehicle of the first family near the vehicle of the second family.

17. A matching method, comprising:
    transmitting input data from a terminal device of a first member who is a member of a first family staying in a vehicle to a control device, the input data indicating a family composition and a family stress for the first family;
    searching a database in which data indicating the family composition and the family stress for each of a plurality of families staying in individual vehicles is registered, using the input data as a search key,
    selecting a second family from the families by the control device based on a search result obtained; and
    transmitting notification data that notifies the first member of information for establishing a relationship with a second member who is a member of the second family selected, from the control device to a terminal device of the first member.

18. The matching method according to claim 17, wherein the second family is at least one family that has something in common with the first family in both the family composition and the family stress indicated by the data registered in the database.

19. The matching method according to claim 17, wherein the notification data is data for notifying the first member of contact information for communicating with the second member.

20. The matching method according to claim 17, wherein the notification data is data for notifying the first member of position information indicating a parking position of the vehicle of the first family so as to park the vehicle of the first family near the vehicle of the second family.

* * * * *